(12) United States Patent
Chaudhuri et al.

(10) Patent No.: US 7,282,573 B2
(45) Date of Patent: Oct. 16, 2007

(54) PROCESS FOR MAKING METAL ACETYLACETONATES

(75) Inventors: Mihir Kanti Chaudhuri, Assam (IN); Sanjay Kumar Dehury, Assam (IN); Siddhartha Sankar Dhar, Assam (IN); Upasana Bora, Assam (IN); Boyapati Manoranjan Choudary, Andhra Pradesh (IN); Lakshmi Kantam Mannepalli, Andhra Pradesh (IN)

(73) Assignee: Council of Scientific and Industrial Research, New Delhi (IN)

( * ) Notice: Subject to any disclaimer, the term of this patent is extended or adjusted under 35 U.S.C. 154(b) by 151 days.

(21) Appl. No.: 10/335,103

(22) Filed: Dec. 31, 2002

(65) Prior Publication Data

US 2004/0127690 A1 Jul. 1, 2004

(51) Int. Cl.
*C07F 5/00* (2006.01)
(52) U.S. Cl. ............................ 534/11; 534/16; 556/48; 556/147
(58) Field of Classification Search ................. 534/11, 534/16; 556/48, 147
See application file for complete search history.

(56) References Cited

U.S. PATENT DOCUMENTS 3,972,943 A * 8/1976 Kunstle et al. ............. 568/396
4,337,210 A * 6/1982 van der Maas ............... 556/40
4,338,254 A * 7/1982 van der Maas ............... 556/40

FOREIGN PATENT DOCUMENTS

| EP | 0 027 890 | A1 | 5/1981 |
| EP | 0 028 308 | A1 | 5/1981 |
| EP | 1 044 953 | A1 | 10/2000 |
| EP | 1 044 953 | A1 * | 10/2000 |
| EP | 1044953 | A1 * | 10/2000 |
| WO | WO 01/09218 | A1 * | 2/2001 |

* cited by examiner

*Primary Examiner*—Johann Richter
*Assistant Examiner*—Chukwuma Nwaonicha
(74) *Attorney, Agent, or Firm*—Darby & Darby

(57) ABSTRACT

The present invention provides an improved, economical and environmentally benign process for metal complexes of acetylacetone having the general formula, $M(acac)_n$, wherein M is a metal cation selected from the group consisting of Fe, Co, Ni, Cu, Zn, Al, Ca, Mg, Mo, Ru, Re, U, Th, Ce, Na, K, Rb, Cs, V, Cr, and Mn etc., n is an integer which corresponds to the electrovalence of M, are obtained by reacting the corresponding metal hydroxide, metal hydrated oxide or metal oxide with a stoichiometric amount of acetylacetone and separating the product.

12 Claims, No Drawings

PROCESS FOR MAKING METAL ACETYLACETONATES

FIELD OF THE INVENTION

The present invention relates to a process for the preparation of high quality metal acetylacetonates. More particularly, this invention relates to an improved, economical and environmentally benign process for metal complexes of acetylacetone having the general formula, $M(acac)_n$ wherein M is a metal cation selected from the group consisting of Fe, Co, Ni, Cu, Zn, Al, Ca, Mg, Mo, Ru, Re, U, Th, Ce, Na, K, Rb, Cs, V, Cr, and Mn etc., n is an integer which corresponds to the electrovalence of M, are obtained by reacting the corresponding metal hydroxide, metal hydrated oxide or metal oxide with a stoichiometric amount of acetylacetone (acacH, $C_5H_8O_2$).

BACKGROUND OF THE INVENTION

Metal acetylacetonates are highly efficient catalysts for a wide variety of organic transformations such as oligomerization, polymerization, hydrogenation, isomerization, coupling etc. They are also used in rubber technology for vulcanization, for extraction and separation of metals, as NMR shift reagents, in microelectronic devices, for synthesis of high quality semiconductor materials for optoelectronic devices, for separation of enantiomers, as a source of metal or metal oxides for controlled deposition, as fungicides, in pigments as color stabilizers, as carbon scavengers for diesel fuels, as combustion control catalysts for rocket fuels, and in laser technology. Metal acetylacetonates, often referred as metal chelates, are well known in the art as witnessed for example by U.S. Pat. Nos. 3,231,597 and 3,291,660.

Reference is made to British Patent 289,493 wherein preparation of metal acetylacetonates was carried out by the reaction of excess of acetylacetone or a solution of a solid salt of it in an inert solvent followed by refluxing the metal oxide, hydroxide, carbonate or basic carbonate of the metal. The disadvantages are the reactions are slow with quite poor yields, requirement of inert organic solvent, energy consumption due to necessity for refluxing, use of excess acacH thereby increasing the costs, chances of contamination, and restricted operability due to solubility problem. Reference is made to *J.Chem.Soc.*, 1938, 1254 and *Inorg. Syntheses*, 1946, 2, 119 wherein preparation of metal acetylacetonates was carried out in nonaqueous solution by the reaction of metal salt and acetylacetone. The disadvantage here is that this method is applicable to those metal salts only that are soluble in the chosen nonaqueous solvent.

Reference is also made to *Compt. Reid.*, 1943, 157,30 wherein preparation of metal acetylacetonates was carried out by the reaction of acetylacetone with a metal oxide, hydroxide, carbonate or basic carbonate in aqueous solution. The disadvantages are that the reaction is very sluggish, the possibility of contamination with the by-products exists, and excess acacH is used thereby increasing the costs of the process. Reference is made to *J.Chem.Soc.*, 1947, 1084 and *J.Am.Chem.Soc.*, 1948, 70, 3142 wherein metal acetylacetonates were prepared by the reaction of acetylacetone with a metal oxide, hydroxide, carbonate or basic carbonate in aqueous solution and controlling the pH of the solution by gradual addition of a weak base such as ammonia. The disadvantages are that unless care is exercised there is high probability of the end product being contaminated by metal hydroxide or basic salt, the use of buffer leading to the addition of extraneous ion, which in turn may contaminate the product. Addition of ammonia may result in high local concentration causing precipitation of metal hydroxide of basic diketone derivatives.

Reference is made to *J.Chem.Soc.*, 1925, 2379 and *J.Org.Chem.*, 1948, 13, 249 wherein preparation of metal acetylacetonates was carried out in anhydrous inert medium containing the ligand and metal. The disadvantage is that this method is applicable to the synthesis of only active metal derivatives such as alkali metals, alkaline earth metals and the process is expensive since anhydrous solvents are used. Reference is made to *Anal.Chem.*, 1951, 23,174 wherein $Mn(acac)_3$ was prepared by the reduction of $MnCl_4$ by acetylacetone. The disadvantages are requirement of unstable Mn(IV) compound, involvement of an extra preparation step and contamination of the end product by chloride.

Reference is also made to *J. Am. Chem. Soc.*, 1951, 73, 4416 and *Inorg. Syntheses*, 1966,7,183 wherein $Mn(acac)_3$ was prepared by air or chlorine oxidation of a basic solution of $Mn^{2+}$ in the presence of acacH, or by $KMnO_4$ oxidation of $Mn^{2+}$ in the presence of acacH and a large excess of sodium acetate. The disadvantages are the deleterious effect of alkali on the end product, contamination by chloride ions, or by sodium acetate. Reference is made to *J.Am.Chem.Soc.*, 1953, 75, 2446 wherein uranium(VI) (c.f. $UO_2^{2+}$) acetylacetonate was prepared by using sodium hydroxide for adjusting the pH conducive to the synthesis. The disadvantages are contamination of the product because of the use of a large quantity of alkali and involvement of extra purification steps. Reference is also made to *J.Am.Chem.Soc.*, 1953, 75, 2736 wherein preparation of metal acetylacetonates was carried out by the reaction of soluble salt of acetylacetone with a soluble salt of metal. The disadvantages are prior preparation of the salt of acetylacetone and reactions being conducted at higher pH causing the formation of by products such as $M(acac)_X$, $M(acac)OH$ and $M(acac)_3^-$. Reference is made to *Anal.Chem.*, 1953, 25,881 and 1954, 26, 375 wherein preparation of metal acetylacetonates was carried out by incorporating solvent extraction. An immiscible liquid was added to the reaction mixture to extract the desired metal. The disadvantage is that some of the side products formed are also extracted with the pure product due to their partial solubility. Reference is also made to *Inorg. Syntheses*, 1957, 5, 105 wherein the metal acetylacetonates were prepared by the reaction of the metal ion and acetylacetone, i.e., by chelation of the metal ion by the bidentate ligand. As a consequence it releases proton decreasing the pH of the reaction mixture. Unless the metal chelate is highly soluble, the reaction between the metal ion and acetylacetone will come to equilibrium short of completion because of the increase in concentration of free acid in the solution. The pH suitable for the successful synthesis of metal acetylacetonates was ascertained to be 5.5. In order to shift the equilibrium to the right acidity generated, as mentioned above, can be controlled by the use of a suitable buffer. For this reason the use of acetate is recommended for such preparations. In some case homogeneous generation of ammonia in the reaction solution can be achieved by adding urea to the solution and heating. The disadvantage is that the direct reaction of acetylacetone and a salt in water is limited by the low solubility of metal acetylacetonate. And there is a definite possibility of contamination of the product by the buffer, ammonia, or acetate.

Reference is made to U.S. Pat. No. 3,946,057 wherein the preparation of metal acetylacetonates was achieved from the reaction of acetylacetone with a metal halide or hydroxide thereof in the presence of alkyne oxide and organic solvents.

The disadvantages are contamination by chloride, partial reaction with HCl, expensive alkyne oxide and use of organic solvents. Alkali metal halides have not been found suitable for use in this process. Reference is made to U.S. Pat. No. 4,008,260 wherein the Co (II) acetylacetonate was first made and then reacted with acacH in an organic solvent and 30% $H_2O_2$ in higher proportions under reflux. The disadvantages are extra preparation of Co(II) acetylacetonate, use of organic solvents and a high amount of $H_2O_2$ and temperature.

OBJECTS OF THE INVENTION

The main object of the invention is to provide an improved, economical and environmentally benign process for the preparation of metal complexes of acetylacetone.

Still another object of the invention is to provide a process for the preparation of metal complexes of acetylacetone wherein no organic solvent is needed for the reactions.

Still another object of the invention is to provide a process for the preparation of metal complexes of acetylacetone wherein extraneous heating is not generally required.

Another object of the invention is to provide a process for the preparation of metal complexes of acetylacetone wherein the metal hydroxide, hydrated oxide or oxide is directly reacted with acetylacetone to obtain $M(acac)_n$.

Still another object of the invention is to provide a process for the preparation of metal complexes of acetylacetone wherein no waste is produced.

Still another object of the invention is to provide a process for the preparation of metal complexes of acetylacetone wherein no buffer is needed.

Still another object of the invention is to provide a process for the preparation of metal complexes of acetylacetone wherein the products are obtained in very high or quantitative yields.

Yet another object of the invention is to provide a process for the preparation of metal complexes of acetylacetone wherein the products obtained are highly pure.

SUMMARY OF THE INVENTION

The present invention provides an improved, economical and environmentally benign process for metal complexes of acetylacetone having the general formula, $M(acac)_n$ wherein M is a metal cation selected from the group consisting of Fe, Co, Ni, Cu, Zn, Al, Ca, Mg, Mo, Ru, Re, U Th, Ce, Na, K, Rb, Cs, V, Cr, and Mn etc., n is an integer which corresponds to the electrovalence of M, are obtained by reacting the corresponding metal hydroxide, metal hydrated oxide or metal oxide with a stoichiometric amount of acetylacetone at temperature in the range of 20 to 75° C. and separating the product by known methods.

Accordingly the present invention provides an improved, economical and environmentally benign process for preparation of metal complexes of acetylacetone of the formula $M(acac)_n$ wherein M is a metal cation, n is an integer which corresponds to the electrovalence of M, by reacting the a metal source selected from the group consisting of the corresponding metal hydroxide, metal hydrated oxide and metal oxide with a stoichiometric amount of acetylacetone and separating the obtained metal acetylacetonate.

In one embodiment of the invention, the metal is selected from the group consisting of selected from the group consisting of Fe, Co, Ni, Cu, Zn, Al, Ca, Mg, Mo, Ru, Re, U, Th, Ce, Na, K, Rb. Cs, V, Cr, and Mn.

In another embodiment of the invention, the reaction is carried out at a temperature in the range of 20 to 75° C.

In another embodiment of the invention, the metal source is directly reacted with acetylacetone to obtain $M(acac)_n$.

In another embodiment of the invention, the metal hydroxide or oxide is directly reacted with acetylacetone at a temperature in the range of 40 to 50° C., which is obtained by the exothermicity of the reaction or by external heating.

In another embodiment of the invention, the metal hydroxide comprises the reaction product of the corresponding metal salt with a base selected from KOH and NaOH of 5-25% aqueous solution.

In another embodiment of the invention the obtained metal hydroxide is thoroughly washed free of alkali with excess of deionised water.

In another embodiment of the invention, the metal source is directly reacted with acetylacetone in the presence of hydrogen peroxide to obtain the product in higher oxidation state $M(acac)_{n+1}$.

In a further embodiment of the invention, M is Cobalt and the product obtained is $Co(acac)_3$.

In another embodiment of the invention, the metal oxide, metal hydroxide or oxometallate is directly reacted with the requisite amount of acetylacetone to obtain the product containing the metal at a lower oxidation state.

In a further embodiment of the invention, M is manganese and the product obtained is $Mn(acac)_3$.

In another embodiment of the invention, the reaction is carried out in the absence of an organic solvent and a buffer.

DETAILED DESCRIPTION OF THE INVENTION

The novelty of the invention lies in the use of the following general methodologies for the preparation of metal acetylacetonates, one based on Acid-base and the other on Electron-Transfer (Redox) concept.

1. Acid-Base Reaction

Because of the presence of active methylene hydrogen, acetylacetone shows weak acidity (pH~5). An interaction of acetylacetone with metal hydroxide or hydrated metal oxide led to an acid-base type of reaction thereby bringing about coordination of acetylacetonate with the metal center. A large number of metal acetylacetonates have been successfully synthesized in high yields and purity using this methodology.

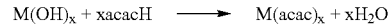

$$M(OH)_x + x\,acacH \longrightarrow M(acac)_x + xH_2O$$

A freshly prepared alkali-free metal hydroxide was allowed to react with acetylacetone. Consequently, a clear and colored solution or in some cases a microcrystalline product was obtained. The pH of the reaction solution recorded was found to lie at 5-6. The solution or the microcrystalline product was cooled in an ice water bath and the product was separated by filtration or centrifugation in high yield.

2. Redox Reaction

While the coordination and chelating ability of acetylacetone ligand was already an established fact, the capability of acetylacetone to participate in Electron-Transfer reactions with higher valent metals is unknown. A new general methodology was developed in that the synthesis of metal acetylacetonates in relatively low oxidation states should be possible by an effective Electron-Transfer reaction between an appropriate metal at its higher oxidation state and acetylacetone. A number of acetylacetonates have been prepared from the reaction of the corresponding metal in higher oxidation state and acetylacetone.

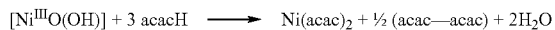

Although the fact that acetylacetone has acted as a reducing agent is amply clear, a direct evidence to this assertion was also obtained from the isolation of $\alpha,\alpha,\beta,\beta$-tetraacetylethane as the oxidized product of acetylacetone as shown below:

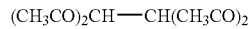

Also significant is to mention that the pH of the reaction solution was spontaneously maintained to 5 or 5.5 in both the methods thereby providing a condition conducive to the successful synthesis of the desired compound. Thus the invention provides an economically viable process for metal acetylacetonates.

Scientific explanation: The principle of the present invention is to prepare metal acetyacetonates by an improved, economical and environmentally benign process. The following broad general methodologies have been developed to provide an easy access to metal acetylacetonates of diverse stoichiometries. While one protocol is based on Acid-Base reaction concept, the other stands on Redox concept.

The basis of the Acid-Base reaction is the following. Because of the presence of active methylenic hydrogen, acetylacetone shows weak acidity (pH~5). An interaction of acetylacetone (acacH) with metal hydroxide or hydrated metal oxide (basic) allows an Acid-Base reaction to take place leading to the formation of the desired chelated or ionic metal acetylacetonates in very high yields and purity.

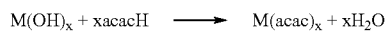

Typically, a freshly prepared alkali-free metal hydroxide or hydrated metal oxide is directly reacted with stoichiometric amount of distilled acetylacetone to afford crystalline acetylacetonates of metals. The reactions are generally exothermic enough thereby rendering an extraneous heating redundant. The pH of the reaction solution lie at 5-6.

Interestingly, acetylacetone (acacH) has been also known to have reducing property, although the oxidized product formed in such a reaction was not known until 1983 (our paper J.Chem. Soc. Dalton trans., 1983, 2561). It has been shown now that a higher valent hydroxo, an oxo-metal or any other suitable metal species is capable of effectively participating in electron-transfer reaction between the higher valent metal and acacH, thereby reducing the metal ion to a relatively lower oxidation state. The metal ion so formed is then trapped by the acetylacetonate (acac⁻, $C_5H_7O_2^-$), made available in the reaction solution by providing the requisite amount of the ligand-cum reducing agent at the beginning of the reaction, thereby giving the desired metal acetylacetonate in very high yields and purity. Here again, the pH of the reaction is recorded to be 5.5 and no extraneous heating is required in some cases, as the reactions are exothermic.

The following examples are given by way of illustration of the present invention and therefore should not be construed to limit the scope of the present invention.

EXAMPLE 1

Cobalt(II) Acetylacetonatedihydrate, Co(acac)$_2$.2H$_2$O or Co(C$_5$H$_7$O$_2$)$_2$.2H$_2$O Cobalt (II) acetate tetrahydrate (10 g, 40.1 mmol) was dissolved in 200 mL of water in a 500 mL beaker. A 20% aqueous solution of KOH was slowly added with constant stirring. Initially a blue colored precipitate formed which was stirred for 10 min and allowed to stand for half an hour. The blue color of the precipitate turned green and finally to a flesh pink color providing the metal hydroxide, as desired (pH~8). The metal hydroxide was washed free of alkali by repeated washing with water by decantation, finally followed by filtration through Whatman No.42 filter paper and again washing twice with cold water. Then the precipitate was quantitatively transferred into a 100 mL beaker. Distilled acetylacetone (9.1 mL, 88.2 mmol) was added to the precipitate and mixed thoroughly with a glass rod. An exothermic reaction set in leading to the formation of pink shiny crystals of Co(acac)$_2$. 2H$_2$O. It was allowed to stand at room temperature for 30 min and then placed in an ice-water bath for 15 min. The compound was filtered through Whatman No.42 filter paper and dried in vacuo over fused CaCl$_2$. Yield: 10 g (85%). Melting Point: 170-172° C. Chemical analyses, IR and Mass spectra of the compound match well with those reported in literature. In place of Cobalt (II) acetate tetrahydrate, any other soluble Cobalt (II) salt can be used. Analytical data: The compound analyzed correctly C$_{10}$ H$_{18}$ CoO$_6$: Calc. M, 293: C, 40.96: H, 6.14: Co, 20.14%. Found. M (Mass spectrum), 293: C, 40.92: H, 6.14: Co, 20.24%

EXAMPLE 2

Nickel (II) Acetylacetonate Dihydrate, Ni(acac)$_2$.2H$_2$O or Ni(C$_5$H$_7$O$_2$)$_2$.2H$_2$O Nickel (II) chloride hexahydrate (15 g, 68.18 mmol) was dissolved in 200 mL of water in a 500 mL beaker. A 20% aqueous solution of KOH was slowly added with constant stirring to precipitate the metal as its hydrated oxide. The addition of alkali was continued till the pH of the solution was raised to ca 8. The metal hydroxide was washed free of alkali by repeated washing with water by decantation, finally followed by filtration through Whatman No. 42 filter paper and again washing twice with cold water. Then the precipitate was quantitatively transferred into a 250 mL beaker. Distilled acetylacetone (15.45 mL, 149.9 mmol) was added to the precipitate and mixed thoroughly with a glass rod. An exothermic reaction set in leading to the formation of blue-green shiny crystals of Ni(acac)$_2$. 2H$_2$O. The semi solid mass was continuously stirred for 5 to 10 min, allowed to stand at room temperature for 30 min and then placed in an ice-water bath for 15 min. The compound was filtered through Whatman No.42 filter paper and dried in vacuo over fused $CaCl_2$. Yield: 17 g (85%). Melting Point: 230-238° C. The IR and Mass spectra of the compound match very well with those reported in literature. In place of Nickel (II) chloride, any other soluble Nickel (II) salt can be used. Analytical data: The compound analyzed correctly $C_{10}H_{18}NiO_6$: Calc. C, 41.0: H, 6.15: Ni, 20.05%. Found. C, 40.8: H, 6.3: Ni, 20.2%

EXAMPLE 3

Copper (II) Acetylacetonate, Cu (acac)$_2$ or Cu $(C_5H_7O_2)_2$

Copper (II) acetate monohydrate (10 g, 50.09 mmol) was dissolved in 300 mL of water in a 500 mL beaker by warming at 60° C. for 15 min. To the cooled solution, 20% aqueous solution of KOH was slowly added with constant stirring to precipitate the metal as its hydrated oxide. The addition of alkali was continued till the pH of the solution was raised to ca. 8. The metal hydroxide was washed free of alkali by repeated washing with water by decantation, finally followed by filtration through Whatman No 42 filter paper and again washing twice with cold water. Then the precipitate was quantitatively transferred into a 100 mL beaker. Distilled acetylacetone (11.06 mL, 110 mmol) was added to the precipitate and mixed thoroughly with a glass rod. An exothermic reaction set in leading to the formation of blue shiny crystals of $Cu(acac)_2$. It was allowed to stand at room temperature for 30 min and then placed in an ice-water bath for 15 min. Compound was filtered through Whatman No.42 filter paper and dried in vacuo over fused $CaCl_2$. Yield: 12.49 g (95.25%) Melting Point: 279-283° C. Chemical analyses, IR and Mass spectra of the compound match well with those reported in literature. In place of copper (II) acetate, any other soluble copper (II) salt can be used. Analytical data: The compound analyzed correctly $C_{10}H_{14}CuO_4$: Calc. M, 261: C, 45.97: H, 5.36: Cu, 24.32%. Found: M(mass spectrum) 261: C, 45.90: H, 5.36: Cu, 24.33%

EXAMPLE 4

Zinc (H) Acetylaceonate, $Zn(acac)_2 \cdot xH_2O$ or Zn $(C_5H_7O_2)_2 \cdot xH_2O$ Zinc (II) acetate dihydrate (1 g, 4.6 mmol) was dissolved in 100 mL of water in a 250 mL beaker. A 5% aqueous solution of NaOH was slowly added with constant stirring to precipitate the metal as $Zn(OH)_2$. The metal hydroxide was washed free of alkali by repeated washing with water by decantation of the supernatant liquid followed by centrifugation. Distilled acetylacetone (1 mL, 9.7 mmol) was added to the centrifuge tubes containing $Zn(OH)_2$. An immediate reaction set in leading to the formation of white shiny crystals of $Zn(acac)_2 \cdot xH_2O$. The compound was quantitatively transferred to Whatman No.42 filter paper, dried first by pressing between the folds of the filter paper and then in vacuo over fused $CaCl_2$. Yield: 0.99 g (83%) (Considering $Zn(acac)_2 \cdot xH_2O$ with x=0) Melting Point: 132-138° C. The IR and Mass spectra of the compound match very well with those reported in literature. In place of Zinc (II) acetate dihydrate, any other soluble zinc (II) can be used. Analytical data: The compound analyzed correctly $C_{10}H_{14}ZnO_4$: Calc. M, 263: C, 45.63: H, 5.32, Zn, 24.86%. Found. M (mass spectrum) 263: C, 45.65: H, 5.35: Zn, 24.78%

EXAMPLE 5

Aluminium (III) Acetylacetonate, Al(acac)$_3$ or $Al(C_5H_7O_2)_3$

To powdered potash alum (15 g, 31.65 mmol) dissolved in 200 mL of water in a 500 mL beaker, 20% aqueous solution of KOH was slowly added slowly with constant stirring leading to the formation of gelatinous whit precipitate of $Al(OH)_2$. The addition of alkali was continued till the pH of the solution was raised to ca.8. The metal hydroxide was washed free of alkali by repeated washing with water by decantation, finally followed by filtration through Whatman No.42 filter paper and again washing twice with cold water. Then the precipitate was quantitatively transferred into a 100 mL beaker. Distilled acetylacetone (10.76 mL, 104.45 mmol) was added drop wise with stirring and then heated to 50° C. for 15 min on a hot plate with constant stirring. A faintly yellowish white crystalline compound was formed. It was allowed to stand at room temperature for 15 min and then placed in an ice-water bath for 15 min. The compound was filtered through Whatman No.42 filter paper and dried in vacuo over fused $CaCl_2$. Yield: 9.32 g (91%) Melting Point: 194.5-196° C. The IR and Mass spectra of the compound match very well with those reported in literature. In place of potash alum, any other soluble aluminium (III) salt can be used. Analytical data: The compound analyzed correctly $C_{15}H_{21}AlO_6$: Calc. M, 324: C, 55.56: H, 6.48: Al, 8.33%. Found M (mass spectrum): 324: C, 55.48: H, 6.46: Al, 8.41%

EXAMPLE 6

Calcium (II) Acetylacetonatedihydrate, $Ca(acac)_2 \cdot 2H_2O$ or $Ca(C_5H_7O_2)_2 \cdot 2H_2O$ To 200 mL of water taken in a 500 mL beaker kept in an ice bath calcium(II) chloride (10 g, 90.09 mmol) was added in small portions with constant stirring to get a clear solution and allowed to stand for 15 min. A 20% aqueous solution of KOH was slowly added with constant stirring to precipitate the metal as its hydroxide. The addition of alkali was continued till the pH of the solution was raised to ca 8. The metal hydroxide was washed free of alkali by repeated washing with water by decantation, finally followed by filtration through Whatman No.42 filter paper and again washing twice with cold water. Then the precipitate was quantitatively transferred into a 250 mL beaker. Distilled acetylacetone (20.43 mL, 198.19 mmol) was added drop wise with stirring. An exothermic reaction set in leading to the formation of a white crystalline compound $Ca(acac)_2 \cdot 2H_2O$. It was allowed to stand at room temperature for 30 min and then placed on an ice-water bath for 15 min. The compound was filtered through Whatman No.42 filter paper and dried in vacuo over fused $CaCl_2$. Yield 21.27 g (86%) Melting point: 265-267° C. IR and Mass spectra of the compound match very well with those reported in literature. In place of calcium (II) chloride, any other soluble calcium (II) salt can be used. Analytical data: The compound analyzed correctly $C_{10}H_{18}CaO_6$: Calc. M, 274: C, 43.8: H, 6.57: Ca, 14.6%. Found M (mass spectrum) 274: C, 43.7:H, 6.56: Ca, 14.3%

EXAMPLE 7

Magnesium (H) Acetylacetonate Dihydrate,
Mg(acac)$_2$.2H$_2$O or Mg(C$_5$H$_7$O$_2$)$_2$. 2H$_2$O Magnesium (II) chloride hexahydrate (10 g, 49.19 mmol) was dissolved in 200 mL of water in a 500 mL beaker. A 20% aqueous solution of KOH was slowly added with constant stirring to precipitate the metal as its hydroxide. The addition of alkali was continued till the pH of the solution was raised to ca. 8. The metal hydroxide was washed free of alkali by repeated washing with water by decantation, finally followed by filtration through Whatman No 42 filter paper and again washing twice with cold water. Then the precipitate was quantitatively transferred into a 250 mL beaker. Distilled acetylacetone (11.15 mL, 108.21 mmol) was added drop wise with stirring. An exothermic reaction set in leading to the formation of a white crystalline compound Mg(acac)$_2$.2H$_2$O. It was allowed to stand at room temperature for 30 min and then placed on an ice-water bath for 15 min. The compound was filtered through Whatman No.42 filter paper and dried in vacuo over fused CaCl$_2$. Yield: 11.56 g (91%). Melting Point: 266-267° C. IR and Mass spectra of the compound match very well with those reported in literature. In place of Magnesium (II) chloride hexahydrate, any other soluble Magnesium (II) salt can be used. Analytical data: The compound analyzed correctly C$_{10}$H$_{18}$MgO$_6$: Calc.M, 258: C, 46.51: H, 6.97: M, 9.29%. Found. M (mass spectrum) 258: C, 46.52H, 6.97: M, 9.32%

EXAMPLE 8

Iron (III) Acetylacetonate, Fe(acac)$_3$ or Fe(C$_5$H$_7$O$_2$)$_3$

Iron (III) chloride (15 g, 92.47 mmol) was dissolved in 200 mL of water in a 500 mL beaker followed by addition of 20% aqueous solution of KOH in parts with constant stirring to precipitate the metal as its hydroxide. The addition of alkali was continued till the pH of the solution was raised to ca.8. The suspended precipitate was allowed to settle with the supernatant liquid becoming colorless. The flocculent was washed several times with water by decantation, finally by filtration through Whatman No 42 filter paper and again washing twice with cold water. Then the precipitate was quantitatively transferred into a 250 mL beaker. Distilled acetylacetone (30.5 mL, 295.9 mmol) was added to the slurry and mixed thoroughly with a glass rod. The whole mixture was allowed to stand at room temperature for 30 min with occasional stirring. An exothermic reaction set in leading to the formation of deep red shiny crystals of Fe(acac)$_3$. The reaction container was then placed in an ice-water bath for 15 min. The compound was filtered through Whatman No.42 filter paper and dried in vacuo over fused CaCl$_2$. Yield: 28.6 g (87.49%). Melting Point: 180-181° C. IR and Mass spectra of the compound match very well with those reported in literature. In place of Iron (III) chloride, any other soluble Iron (III) salt can be used. Analytical data: The compound analyzed correctly C$_{15}$H$_{21}$FeO$_6$: Calc. M, 353: C. 51.05: H. 5.95: Fe, 15.86%. Found. M (mass spectrum), 353: C, 51.2H, 6.17: Fe, 15.84%

EXAMPLE 9

Cobalt (II) Acetylacetonate, Co(acac)$_3$ or Co(C$_5$H$_7$O$_2$)$_3$

Cobalt (II) acetate tetrahydarte (10 g, 40.1 mmol) was dissolved in 200 mL of water in a 500 mL beaker followed by addition of 20% aqueous solution of KOH with constant stirring to precipitate the metal as its hydroxide. Initially a blue colored precipitate formed which-was stirred for 10 min and allowed to stand for 30 min. He blue color precipitate turned green, finally a flesh pink color providing the metal hydroxide as desired. It was washed free of alkali several times with water by decantation, finally by filtration through Whatman No 42 filter paper and again washing twice with cold water. Then the precipitate was quantitatively transferred into a 250 mL beaker. Distilled acetylacetone (16.5 mL, 160.4 mmol) was added to the precipitate and mixed thoroughly with a glass rod. An exothermic reaction set in leading to the formation of pink shiny crystals of Co(acac)$_2$.2H$_2$O. To this was added 30% hydrogen peroxide (11.36 mL, 100.25 mmol) drop wise with constant stirring. A solid to solid conversion of pink Co(acac)$_3$ took place with the accompanying solution become green. The reaction mixture was heated on a steam bath for complete oxidation of Co(II) to Co(III) and expulsion of hydrogen peroxide. The whole mixture was allowed to stand at room temperature for 30 min with occasional stirring. The reaction container was then placed in an ice-water bath for 15 min. The compound was filtered through Whatman No.42 filter paper and dried in vacuo over fused CaCl$_2$. Yield: 12 g (84.32%) Melting Point: 209° C. The IR and Mass spectra of the compound match very well with those reported in literature. In place of Cobalt (II) acetate tetrahydrate, any other soluble Cobalt(II) salt can be used. Analytical data: The compound analyzed correctly C$_{15}$ H$_{21}$ CoO$_6$: Calc. M, 356: C, 50.56: H, 5.5: Co, 16.54%. Found M (mass spectrum) 356: C, 50.21: H, 6.03: Co, 16.21%

EXAMPLE 10

Potassium Acetylacetonate, K (acac) or K(C$_5$H$_7$O$_2$)

Finely powdered KOH (2.0 g, 3.56 mmol) was dissolved in 2 mL of water taken in a 100 mL beaker and the solution was placed in an ice water bath for 15 min. slowly added with constant stirring to precipitate the metal as its hydrated oxide. To the cold solution distilled acetylacetone (4.02 mL, 3.9 mmol) was added with continuous stirring. A white crystalline compound was precipitated. The whole mixture was allowed to stand at room temperature for 15 min and then placed in an ice-water bath for 15 min. The compound was separated on a filter paper cone, dried by pressing between folds of the filter paper and finally dried in vacuo over fused CaCl$_2$. Yield: 4.61 g (93.8%) Melting Point: >200° C. IR of the compound match well with those reported in literature. Analytical data: The compound analyzed correctly C$_5$H$_7$KO$_2$: Calc. M, 138: C, 43.48: H, 5.07: K, 28.26%. Found. M (mass spectrum) 138: C. 43.53: H, 5.11: K, 28.32%

EXAMPLE 11

Vanadyl Acetylacetonate, VO(acac)$_2$ or VO(C$_5$H$_7$O$_2$)$_2$

To an aqueous suspension of vanadium pentoxide (5 g, 27.49 mmol) in 20 mL of water taken in a 500 mL beaker, 30% hydrogen peroxide (37.37 mL, 329.88 mmol) was added drop wise in an icecold condition and stirred till a clear dark solution is formed. To the dark brown colored solution, distilled acetylacetone (19.84 mL, 192.5 mmol) was added drop wise very carefully with continuous stirring. Vigorous effervescence took place after 15 min. Stirring for a period of 30 min led to a precipitation of a brown colored microcrystalline compound. The reaction mixture was heated at 70° C. for 15 min under stirring. The precipitate turned olive green with shiny crystalline appearance with the solution also turning green. The solution was concentrated by heating on steam bath for 30 min and then placed in an ice-water bath for 15 min. The compound was filtered through Whatman No.42 filter paper, washed with acetone and dried in vacuo over fused $CaCl_2$. Yield: 8.2 g (80%) Melting Point: 250-251° C. Chemical analyses, IR and mass spectra of the compound match well with those reported in literature. Preparation of VO $(acac)_2$ in nearly quantitative yield is possible from ammonium metavanadate, $NH_4VO_3$, instead of $V_2O_5$. Sodium or potassium metavanadate, $NaVO_3$ or $KVO_3$, can also be used for preparation of VO $(acac)_2$. VO $(C_5H_7O_2)_2$: Analysis : Calc.C, 45.28: H, 5.28: V, 19.25%. Found. C, 45.11: H, 5.31: V, 19.32%

EXAMPLE 12

Chromium (III) Acetylacetonate, $Cr(acac)_3$ or Cr $(C_5H_7O_2)_3$

Chromium (VI) oxide (5.0 g, 50 mmol) was added in small portions to 20 mL of water taken in a 100 ML beaker kept in an ice water bath with constant stirring to get a clear solution and allowed to stand for 15 min. To the cold solution distilled acetylacetone (31.8 mL, 308.5 mmol) was added with continuous stirring. The addition of first installment of acetylacetone was made drop wise followed by the remaining. The entire process of addition of acetylacetone was made at ice-cold temperature. The whole mixture was then heated at 55 to 60° C. on steam bath for 30 min during which time the reaction solution was also reduced to two-third of the original volume with precipitation of shiny crystalline violet $Cr(acac)_3$. The compound was filtered under suction and dried in vacuo over fused $H_2SO_4$. Yield: 15.1 g (86.5%) Melting Point: 209-213° C. IR and Mass Spectra of the compound match well with those reported in literature. Preparation can also be done from dichromate or chromates. Analytical data: The compound analyzed correctly $C_{15}H_{21}CrO_6$: Calc. M, 349: C, 51.57: H, 6.07: Cr, 14.88%. Found M (mass spectrum), 349: C, 51.52: H, 6.11: Cr, 14.87%

EXAMPLE 13

Manganese (1H) Acetylacetonate, $Mn(acac)_3$ or $Mn(C_5H_7O_2)_3$

Powdered $KMnO_4$ (5.0 g, 31.7 mmol) was dissolved in minimum amount of water by slight warming over a stem bath and the solution then filtered. Distilled acetylacetone (22.0 mL, 220 mmol) was added to the solution with continuous stirring. A white crystalline compound was precipitated. The whole mixture was stirred for 15 min over steam bath and then allowed to cool for 10 min. Dark brown shiny crystals of $Mn(acac)_3$ was filtered and finally dried in vacuo over fused $CaCl_2$. Yield: 9.7 g (87%). The compound does not have sharp melting point but decomposes at ca.155° C. (dec.). IR and Mass Spectra of the compound match well with those reported in literature. Analytical data: The compound analyzed correctly $C_{15}H_{21}MnO_6$. Calc. M, 352: C, 51.15: H, 6.00: Mn, 15.6% Found. M (mass spectrum), 352: C, 51.1: H, 6.10: Mn, 15.7%

ADVANTAGES OF THE INVENTION

1. The process is economical. No excess of reagents are used.
2. In the Acid-Base methodologies no by-product other than the targeted product and water are produced. In the Red-Ox process the oxidation product of acetylacetone is the only other product that is formed, which can be removed easily.
3. The newer methodologies are environmentally clean and safe to operate.
4. The methods of preparation are very facile.
5. Extraneous heating is not required, in many instances.
6. No buffer is used for the preparations.
7. No heavy metal wastes are produced.
8. The process provides a high quality product.

We claim:
1. A process for preparation of metal complexes of acetylacetone of the formula $M(acac)_n$ wherein M is a metal cation, provided that M is not an alkaline earth metal, Fe, Al, or Co, and n is an integer which corresponds to the electrovalence of M, comprising reacting a metal source selected from the group consisting of the corresponding metal hydroxide, metal hydrated oxide and metal oxide with a stoichiometric amount of acetylacetone in the absence of an organic solvent, and separating the obtained metal acetylacetonate.
2. A process as claimed in claim 1 wherein the metal is selected from the group consisting of Ni, Cu, Zn, Mo, Ru, Re, U, Th, Ce, Na, K, Rb, Cs, V, Cr, and Mn.
3. A processas claimed in claim 1 wherein the reaction is carried out at a temperature in the range of 20 to 750° C.
4. A process as claimed in claim 1 wherein the metal source is directly reacted with acetylacetone to obtain $M(acac)_n$.
5. A process as claimed in claim 1 wherein the metal hydroxide or oxide is directly reacted with acetylacetone at a temperature in the range of 40 to 50° C., which is obtained by the exothermicity of the reaction or by external heating.
6. A process for preparation of metal complexes of acetylacetone of the formula $M(acac)_n$ wherein M is a metal cation, provided that M is not Ca, Mg, Fe, Al, or Co and n is an integer which corresponds to the electrovalence of M, comprising reacting a metal source selected from the group consisting of the corresponding metal hydroxide, metal hydrated oxide and metal oxide with a stoichiometric amount of acetylacetone and separating the obtained metal acetylacetonate;
wherein the metal hydroxide comprises the reaction product of the corresponding metal salt with a base selected from KOH and NaQH of 5-25% aqueous solution.
7. A process as claimed in claim 6 wherein the obtained metal hydroxide is thoroughly washed free of alkali with excess of delonised water before reaction with the acetylacetone.
8. A process as claimed in claim 1 wherein the metal source is directly reacted with acetylacetone in the presence of hydrogen peroxide to obtain the product in higher oxidation state $M(acac)_{n+1}$.
9. A process as claimed in claim 1 wherein the metal oxide, metal hydroxide or oxometallate is directly reacted with the requisite amount of acetylacetone to obtain the product containing the metal at a lower oxidation state.
10. A process .for preparation of metal complexes of acetylacetone of the formula $M(acac)_n$ wherein M is a metal cation, n is an integer which corresponds to the electrovalence of M, comprising reacting a metal source selected from the group consisting of the corresponding metal hydroxide, metal hydrated oxide and metal oxide with a stoichiometric amount of acetylacetone and separating the obtained metal acetylacetonate;

wherein the metal oxide, metal hydroxide or oxometallate is directly reacted with the requisite amount of acetylacetone to obtain the product containing the metal at a lower oxidation state; and wherein the metal is manganese and the product obtained is $Mn(acac)_3$.

11. A process as claimed in claim 1 wherein the reaction is carried out in the absence of a buffer.

12. A process for the preparation of a metal acetylacetonate of the formula $M(acac)_n$ wherein M is a metal cation selected from the group consisting of Ni, Cu, Zn, Mo, Ru, Re, U, Th, Ce, Na, K, Rb, Cs, V. Cr, and Mn, n is an integer which corresponds to the electrovalence of M, said process comprising reacting the corresponding metal hydroxide or metal hydrated oxide or metal oxide with a stoichiometric amount of acetylacetone at a temperature ranging between 20 to 75° C. and in the absence of an organic solvent, and separating the metal acetylacetonate formed.

* * * * *